United States Patent
Meng et al.

(10) Patent No.: US 10,473,525 B2
(45) Date of Patent: Nov. 12, 2019

(54) SPATIALLY RESOLVED OPTICAL EMISSION SPECTROSCOPY (OES) IN PLASMA PROCESSING

(71) Applicant: TOKYO ELECTRON LIMITED, Tokyo (JP)

(72) Inventors: Ching-Ling Meng, Sunnyvale, CA (US); Holger Tuitje, Fremont, CA (US); Yan Chen, Santa Clara, CA (US); Mihail Mihaylov, San Jose, CA (US)

(73) Assignee: TOKYO ELECTRON LIMITED, Tokyo (JP)

(*) Notice: Subject to any disclaimer, the term of this patent is extended or adjusted under 35 U.S.C. 154(b) by 114 days.

(21) Appl. No.: 15/648,035

(22) Filed: Jul. 12, 2017

(65) Prior Publication Data
US 2017/0314991 A1    Nov. 2, 2017

Related U.S. Application Data

(63) Continuation-in-part of application No. 14/530,164, filed on Oct. 31, 2014, now Pat. No. 9,970,818.
(Continued)

(51) Int. Cl.
*G01J 3/443*    (2006.01)
*G01N 21/68*    (2006.01)
*G01N 21/31*    (2006.01)

(52) U.S. Cl.
CPC .............. *G01J 3/443* (2013.01); *G01N 21/31* (2013.01); *G01N 21/68* (2013.01); *G01N 2201/10* (2013.01)

(58) Field of Classification Search
CPC ................................. G01J 3/443; G01N 21/68
See application file for complete search history.

(56) References Cited

U.S. PATENT DOCUMENTS

| | | | |
|---|---|---|---|
| 4,167,677 A * | 9/1979 | Suzki | G03F 9/70 250/548 |
| 4,692,630 A | 9/1987 | Gogol | |

(Continued)

FOREIGN PATENT DOCUMENTS

| | | |
|---|---|---|
| JP | H04-303599 A | 10/1992 |
| JP | 10-261625 A | 9/1998 |

(Continued)

OTHER PUBLICATIONS

Redding, Brandon, et al. "High-resolution and broadband all-fiber spectrometers." Optica 1.3 (2014): 175-180. (Year: 2014).*

(Continued)

*Primary Examiner* — Tri T Ton
*Assistant Examiner* — Rufus L Phillips
(74) *Attorney, Agent, or Firm* — Oblon, McClelland, Maier & Neustadt, L.L.P.

(57) ABSTRACT

Disclosed is a method, system, and apparatus for optical emission measurement. The apparatus includes a collection system for collecting a plasma optical emission spectra through an optical window disposed at a wall of a plasma processing chamber. The optical system includes a mirror configured to scan a plurality of non-coincident rays across the plasma processing chamber; and a telecentric coupler for collecting an optical signal from a plasma and directing the optical signal to a spectrometer for measuring the plasma optical emission spectra.

20 Claims, 9 Drawing Sheets

Related U.S. Application Data

(60) Provisional application No. 61/898,975, filed on Nov. 1, 2013.

(56) References Cited

U.S. PATENT DOCUMENTS

| | | | |
|---|---|---|---|
| 5,353,790 A | 10/1994 | Jacques et al. | |
| 5,483,337 A * | 1/1996 | Barnard | G01N 21/68 356/316 |
| 5,956,138 A | 9/1999 | Slater | |
| 6,201,628 B1 | 3/2001 | Basiji et al. | |
| 6,219,181 B1 * | 4/2001 | Yoneyama | G02B 21/18 359/368 |
| 6,381,008 B1 | 4/2002 | Branagh et al. | |
| 6,661,510 B1 * | 12/2003 | Hanning | G01N 21/0303 250/458.1 |
| 6,958,484 B2 * | 10/2005 | Mitrovic | G01J 3/443 250/216 |
| 7,241,397 B2 | 7/2007 | Fink et al. | |
| 7,591,923 B2 | 9/2009 | Mitrovic et al. | |
| 8,274,645 B2 | 9/2012 | Davis et al. | |
| 8,416,509 B2 | 4/2013 | Yi et al. | |
| 8,513,583 B2 | 8/2013 | Corke et al. | |
| 8,553,218 B2 | 10/2013 | Tinnemans et al. | |
| 2001/0007499 A1 * | 7/2001 | Richert | G01N 21/8901 356/402 |
| 2002/0024669 A1 * | 2/2002 | Danner | G01N 21/211 356/369 |
| 2003/0174325 A1 | 9/2003 | Zhang et al. | |
| 2004/0026035 A1 | 2/2004 | Mitrovic | |
| 2004/0104681 A1 | 6/2004 | Mitrovic | |
| 2009/0251700 A1 | 10/2009 | Venugopal et al. | |
| 2010/0200767 A1 * | 8/2010 | Yi | G01J 3/02 250/423 R |
| 2011/0013175 A1 | 1/2011 | Davis et al. | |
| 2011/0222058 A1 * | 9/2011 | Kim | G01J 3/443 356/316 |
| 2013/0141720 A1 * | 6/2013 | Park | G01J 3/443 356/316 |
| 2015/0116708 A1 * | 4/2015 | Spriggs | G01N 15/0211 356/336 |
| 2015/0124250 A1 | 5/2015 | Bao et al. | |

FOREIGN PATENT DOCUMENTS

| | | |
|---|---|---|
| JP | 2005-328050 A | 11/2005 |
| JP | 2008-199014 A | 8/2008 |
| JP | 2013-021321 A | 1/2013 |
| WO | WO 2013/029957 A2 | 3/2013 |
| WO | WO 2013/095776 A1 | 6/2013 |

OTHER PUBLICATIONS

Kagaku Jiten, Japan, Tokyo Kagaku Dojin, Oct. 1, 1994, 1$^{st}$ edition, p. 505.

Office Action dated Mar. 14, 2017 in corresponding JP Patent Application No. 2016-527330 (with English translation); 10 pgs.

Master's Thesis of Jae-Wook Lee, presented at University of California, Berkeley, on Jul. 1, 2000.

Shannon, et al., "A spatially resolved optical sensor for plasma etch monitoring" Appl. Phys. Lett, vol. 71, No. 11, 1997, pp. 1467-1468.

Excerpt from Gary Selwyn, "Optical Diagnostic Techniques for Plasma Processing", AVS Press, 1993, Relevant chapter 3 on optical emission spectroscopy (OES) is provided, along with title and bibliographic information pages.

International Patent Application No. PCT/US2014/063565 "International Search Report and Written Opinion," dated Jan. 29, 2015, International Filing Date Oct. 31, 2014.

Office Action dated May 23, 2017, in Korean Patent Application No. 10-2016-7014192 (with English-language translation).

International Search Report and Written Opinion dated Dec. 7, 2018 in Application No. PCT/US2018/041637, citing documents AA, AC, AD and AO therein, 11 pages.

\* cited by examiner

SPATIALLY RESOLVED OPTICAL EMISSION SPECTROSCOPY (OES) IN PLASMA PROCESSING

CROSS REFERENCE TO RELATED APPLICATIONS

The present application is a continuation-in-part of U.S. patent application Ser. No. 14/530,164 entitled "SPATIALLY RESOLVED OPTICAL EMISSION SPECTROSCOPY (OES) IN PLASMA PROCESSING" (Ref. No. TTI-242), filed on Oct. 31, 2014, the entire contents of which are herein incorporated by reference which is based and claims the benefit of and priority to U.S. Provisional Patent Application No. 61/898,975, entitled "SPATIALLY RESOLVED OPTICAL EMISSION SPECTROSCOPY (OES) IN PLASMA ETCHING" (Ref. No. TTI-242PROV), filed on Nov. 1, 2013.

BACKGROUND OF THE INVENTION

Field of the Invention

The present invention relates to a method, computer method, system, and apparatus for measuring concentrations of chemical species in semiconductor plasma processing using plasma optical emission spectroscopy (OES). Specifically, it relates to determining two-dimensional distributions of plasma optical emissions from which two-dimensional distributions of chemical species concentrations can be determined.

Description of Related Art

Production of semiconductor devices, displays, photovoltaics, etc., proceeds in a sequence of steps, each step having parameters optimized for maximum device yield. In plasma processing, among the controlled parameters strongly affecting yield is the chemistry of the plasma, and particularly the local chemistry of the plasma, i.e. the local concentrations of various chemical species in the plasma environment proximate the substrate being processed. Certain species, particularly transient chemical species, such as radicals have a great influence on the plasma processing outcome, and it is known that elevated local concentrations of these species can produce areas of faster processing, which may lead to nonuniformities in the processing steps and ultimately the devices being produced.

The chemistry of a plasma process is controlled in a direct or indirect manner through the control of a large number of process variables, such as one or more RF or microwave powers supplied to excite the plasma, the gas flows and kinds of gases supplied to the plasma processing chamber, the pressure in the plasma processing chamber, the type of substrate being processed, the pumping speed delivered to the plasma processing chamber, and many more. Optical emission spectroscopy (OES) has proven itself as a useful tool for process development and monitoring in plasma processing. In optical emission spectroscopy, the presence and concentrations of certain chemical species of particular interest, such as radicals, is deduced from acquired optical (i.e. light) emission spectra of the plasma, wherein the intensities of certain spectral lines and ratios thereof correlate to the concentrations of chemical species. A detailed description of the technique can be found in e.g. G. Selwyn, "Optical Diagnostic Techniques for Plasma Processing", AVS Press, 1993, and will not be repeated here, for brevity.

While the use of optical emission spectroscopy has become relatively commonplace, particularly in plasma process development, it is usually done by acquiring optical emission spectra from a single elongated volume within the plasma, inside the plasma processing chamber. The precise shape and size of this volume is determined by the optical system used to collect the optical emission from the plasma. Such collection of the optical emission signal inherently results in averaging of the plasma optical emission spectra along the length of this elongated volume, also known as a ray, and thus all the information about local variations of the plasma optical emission spectra, and thus also local variations of chemical species concentrations, are generally lost.

In development of plasma processes, and indeed even in development of new and improved plasma processing systems, it is useful to know the two-dimensional distribution of chemical species of interest above the substrate being processed, so changes in the system design and/or process parameters can be made to minimize variations of the processing outcome across the substrate, for example. A further application of the plasma optical emission spectroscopy technique is in determining the endpoint of a plasma processing step by monitoring the evolution of and abrupt change of chemical species present in the plasma that is associated with e.g. an etching step reaching a substrate layer of different chemical composition that the one that was etched during the etching process. The ability to determine the plasma processing step endpoint across the entire surface of the substrate contributes to increased device yield because of not terminating the plasma processing step prematurely.

One technique extensively used in other areas of technology, e.g. X-ray tomography, to determine a spatial distribution of a variable from known integrated measurements along multiple rays traversing the area of interest is tomographic inversion, using the Abel transform, or Radon transform. However, to be effective, this technique requires a large amount of acquired data, i.e. a large number of rays, which is impractical in a semiconductor processing tool that has limited optical access to the plasma through one or a small number of windows or optical ports built into the plasma processing chamber wall. Tomographic techniques are generally also very computationally intensive. It has also been found that local variations of chemical species concentrations are of a generally smooth nature, without any abrupt gradients in both the radial, and even more so in the circumferential (i.e. azimuthal) direction. Thus, it would be advantageous to have a simple, fast, and relatively low cost plasma optical emission spectroscopy technique and system that is capable of acquiring the two-dimensional distributions of plasma optical emission spectra without the overhead involved in tomographic approaches to OES measurements.

Most notably, while the variations in the circumferential direction may be small, they are not nonexistent, as some prior techniques presume, and the ideal technique and system would still have to be able to reliably capture these variations.

SUMMARY OF THE INVENTION

An aspect of the invention includes an apparatus for optical emission measurement that comprises a collection system for collecting a plasma optical emission spectra through an optical window disposed at a wall of a plasma processing chamber. The optical system includes a mirror configured to scan a plurality of non-coincident rays across the plasma processing chamber; and a telecentric coupler for collecting an optical signal from a plasma and directing the optical signal to a spectrometer for measuring the plasma optical emission spectra.

An alternative embodiment includes a plasma optical emission measurement system that comprises a plasma processing chamber; an optical window disposed on a wall of the plasma processing chamber; a collection system for collecting plasma optical emission spectra through the optical window; a spectrometer coupled to the collection system for measuring the plasma optical emission spectra. The collection system includes a mirror configured to scan a plurality of non-coincident rays across the plasma processing chamber, and a telecentric coupler for collecting an optical signal from a plasma and directing the optical signal to the spectrometer.

Yet another embodiment of the invention includes a method for optical emission measurement that comprises depositing an optical window at a wall of a plasma processing chamber; providing a collection system for collecting plasma optical emission spectra through the optical window, the collection system including a mirror and a telecentric coupler; scanning a plurality of non-coincident rays across the plasma processing chamber using the mirror; collecting an optical signal from a plasma via the telecentric coupler; and directing the optical signal to a spectrometer for measuring the plasma optical emission spectra.

BRIEF DESCRIPTION OF THE DRAWINGS

A more complete appreciation of the invention and many of the attendant advantages thereof will become readily apparent with reference to the following detailed description, particularly when considered in conjunction with the accompanying drawings, in which.

DETAILED DESCRIPTION OF EXEMPLARY EMBODIMENTS

In the following description, in order to facilitate a thorough understanding of the invention and for purposes of explanation and not limitation, specific details are set forth, such as particular geometries of a plasma optical emission spectroscopy (OES) system, and descriptions of various components and processes. However, it should be understood that the invention may be practiced in other embodiments that depart from these specific details.

In the description to follow, the term substrate, which represents the workpiece being processed, may be used interchangeably with terms such as semiconductor wafer, liquid crystal display (LCD) panel, light-emitting diode (LED), photovoltaic (PV) device panel, etc., the processing of all of which falls within the scope of the claimed invention.

Reference throughout this specification to "one embodiment" or "an embodiment" means that a particular feature, structure, material, or characteristic described in connection with the embodiment is included in at least one embodiment of the invention, but do not denote that they are present in every embodiment. Thus, the appearances of the phrases "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Various operations will be described as multiple discrete operations in turn, in a manner that is most helpful in understanding the invention. However, the order of description should not be construed as to imply that these operations are necessarily order dependent. In particular, these operations need not be performed in the order of presentation. Operations described may be performed in a different order than the described embodiment. Various additional operations may be performed and/or described operations may be omitted in additional embodiments.

Figure 1:
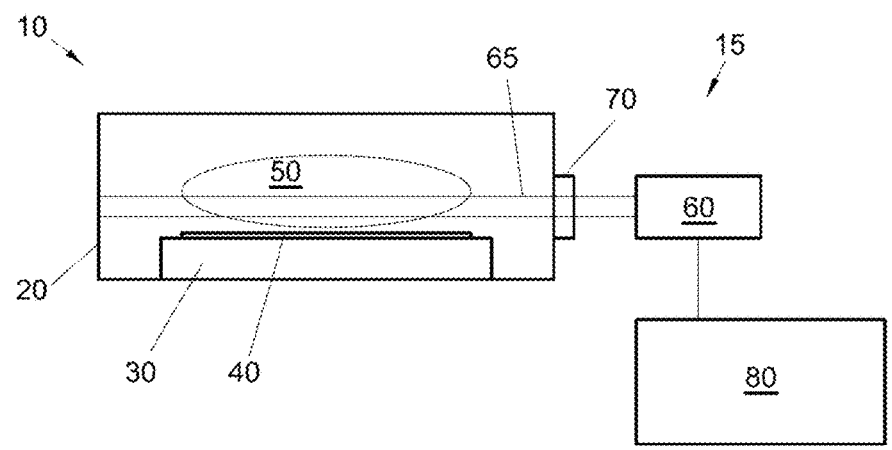
FIG. 1 is a side view schematic of a plasma processing system equipped with an optical emission spectroscopy (OES) measurement system in accordance with an embodiment.

FIG. 1 shows an embodiment of a plasma processing system 10 equipped with a plasma optical emission spectroscopy (OES) system 15. Plasma processing system 10 comprises plasma processing chamber 20, inside which a substrate holder 30 is disposed, such as an electrostatic chuck, for receiving a substrate 40 to be processed. Radio frequency (RF) and/or microwave power is supplied to the plasma processing chamber 20 (not shown) to ignite and sustain a plasma 50 proximate the substrate 40, wherein the energetic chemical species from the plasma 50 are used to perform a plasma processing step on substrate 40. Processing gases are flown into the plasma processing chamber 20 (not shown) and a pumping system is provided (not shown) to maintain a vacuum in the plasma processing chamber 20, at a desired process pressure. Examples of plasma processing steps include plasma etching, plasma-enhanced chemical vapor deposition (PECVD), plasma-enhanced atomic layer deposition (PEALD), etc. The system and method described herein are applicable to any kind of plasma processing.

The plasma optical emission spectroscopy (OES) system 15 is used to acquire plasma optical emission spectra via at least one optical detector 60, which communicates the acquired plasma optical emission spectra to and is controlled by controller 80. Controller 80 may be a general purpose computer, and may be located proximate to plasma processing system 10, or may be located remotely, and connected via an intranet or internet connection to optical detector 60.

Optical detector 60 has optics configured in such a way that it collects plasma optical emissions from an elongated, generally pencil-shaped volume of space 65 within the plasma 50. Optical access to the plasma processing chamber is provided by optical window 70. Optical window 70 can comprise a material such as glass, quartz, fused silica, or sapphire, depending on the application and how aggressive the chemistry of the plasma 50 is. The volume 65, hereinafter referred to as a "ray" 65, defines the portion of space from which the plasma optical emission spectra are collected, and the collected spectra represent an integral of contributions to the collected plasma optical emission spectrum from all points located along and within the ray 65. It should be noted that depending on the geometry and configuration of optical detector 60, the contributions of each point within the ray 65 will not be equal, but are weighted and governed by the optical efficiency (to be discussed in more detail later). In a typical configuration, the ray 65 is oriented substantially parallel with the surface of substrate 40 and is maintained at a small distance from the surface of substrate 40, so as to reduce optical interference from the substrate surface, yet is kept close enough to the substrate 40 to sample the plasma chemistry proximate the substrate surface.

Controller 80, as mentioned before, is used to control the plasma optical emission spectroscopy system 15, and to also compute the (1) plasma optical intensity distribution as a function of spatial location and wavelength, and to compute (2) the spatial distribution of chemical species of interest from the computed plasma optical intensity distribution. This information can then be used for process development, plasma processing tool development, in-situ plasma process monitoring, plasma process fault detection, plasma process endpoint detection, etc.

Figure 2:
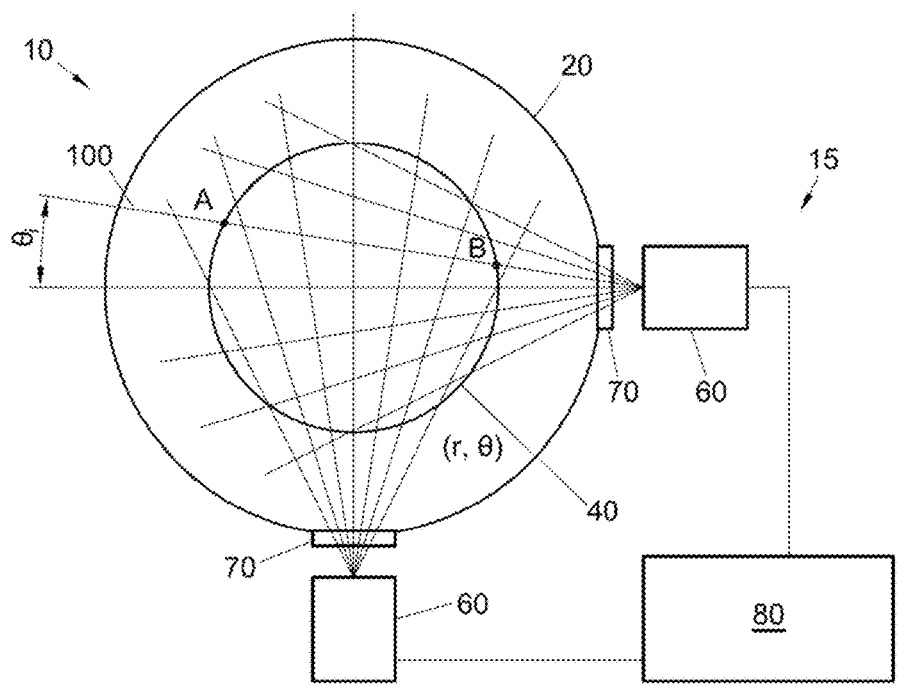
FIG. 2 is a top view schematic of the plasma processing system equipped with the OES measurement system in accordance with an embodiment.

FIG. 1 shows one ray 65 traversing the plasma 50 located within the plasma processing chamber 20, proximate substrate 40 being processed. In an embodiment of the invention, multiple rays 100 can be used to sample the plasma optical emission spectra, as shown in FIG. 2, which shows the top schematic view of the plasma processing system 10 of e.g. FIG. 1. In the exemplary embodiment of FIG. 2, two optical detectors 60 are used to collect plasma optical emission spectra, each from 7 rays 100. The rays 100 need to be non-coincident such that the largest amount of spatial information is acquired from the plasma 50 above substrate 40. The number of rays 100 per optical detector 60 can vary from 2 to 9, and higher. Also, in another embodiment, where optical access is provided to plasma processing chamber 20 by only a single optical window 70, a single optical detector 60 can be used with its associated fan of rays 100. Alternatively, a third or more optical detectors, each with an associated ray fan, may be used. The angle of each ray 100 is defined with respect to the centerline of its optical detector 60, as $\theta$. Every point within the plasma processing chamber can be defined by its polar coordinates, i.e. (r,θ), as shown in FIG. 2.

As will be described in greater detail later, depending on the configuration of optical detector 60, all plasma optical emission spectra from the associated fan of rays 100 can be collected simultaneously. This is suitable for embodiments of optical detector 60 with multiple optical systems and channels, allowing simultaneous collection from all rays 100. Alternatively, the plasma optical emission spectra can be acquired sequentially along rays 100 associated with an optical detector 60. The latter is suitable in scanning embodiments, where plasma optical emission spectra are collected as the ray 100 is scanned from one angle $\theta$ to another. Understandably, this scanning and acquisition needs to occur fast enough such that rapid changes in the plasma chemistry can be detected across the entire substrate.

Figure 3:
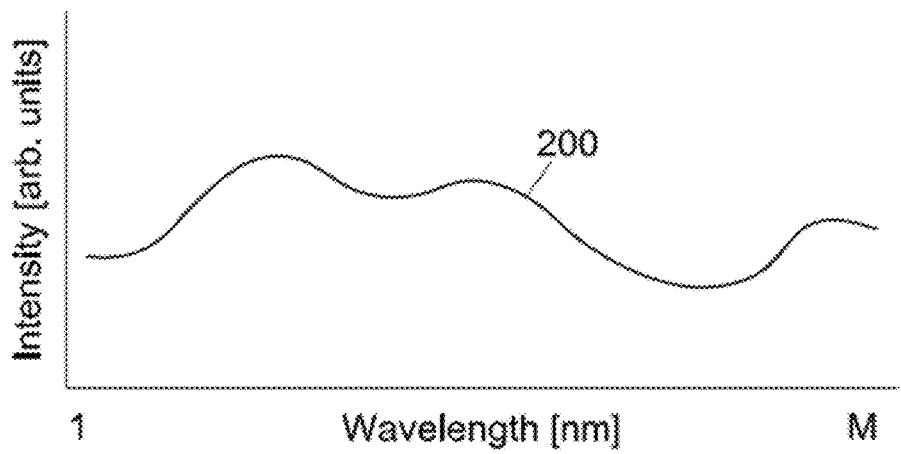
FIG. 3 is an exemplary plasma optical emission spectrum acquired using the OES measurement system in accordance with an embodiment.

FIG. 3 shows an example plasma optical emission spectrum acquired from one ray 100, at angle $\theta$, using one optical detector 60. In the spectrum, intensities of M wavelengths are collected, typically ranging from about 200 nm to about 800 nm. CCDs of typical spectrometers employed for optical emission spectroscopy have 4096 pixels spanning the wavelength range, but the number of pixels can vary as low as 256 and as high as 65536, depending on the application and required resolution of the collected spectra.

Plasma optical emission spectra collected by optical detectors 60 from their associated fans of rays 100 are communicated to controller 80, which is used to further process the communicated data to compute the spatial distribution of plasma optical emission, and from there the spatial distribution of chemical species concentrations. An aspect of the present invention is an algorithm for fast calculation of the spatial distribution of plasma optical emissions for each wavelength, which allows in-situ monitoring of plasma processes, for endpoint detection, fault detection, etc.

Figure 4:
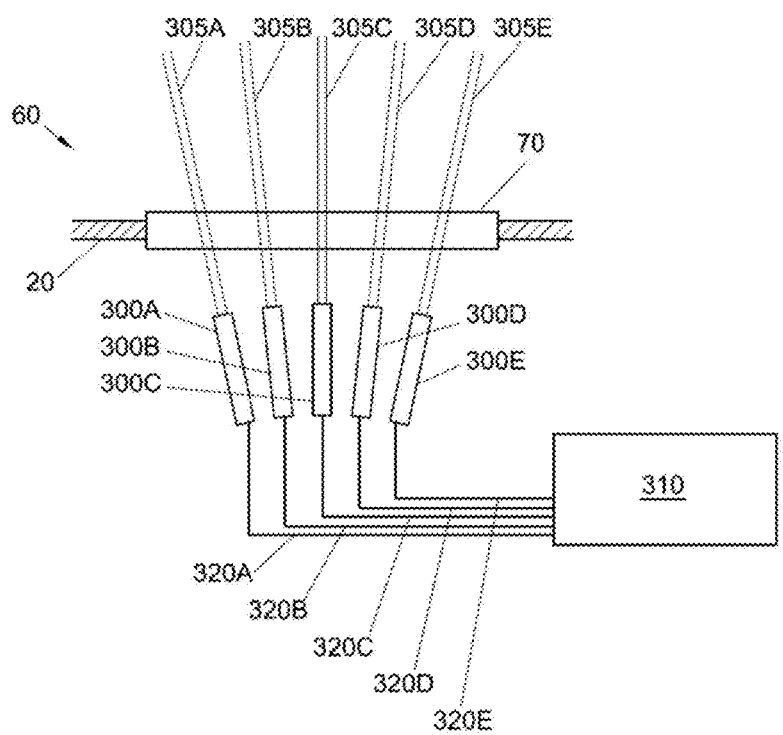
FIG. 4 is a schematic of an optical system for use in the OES measurement system, in accordance with an embodiment.

FIG. 4 shows an embodiment of optical detector 60 wherein a single multi-channel spectrometer 310 is used to collect plasma optical emission spectra from rays 305A-E simultaneously. The exemplary embodiment shown here has 5 rays 305A-E, for clarity, but the number can vary from 2 to 9, and even higher than 9. The optical detector 60 comprises optical systems 300A-E for each ray 305A-E, all located proximate optical window 70 mounted on the wall of plasma processing chamber 20. Rays 305A-E are arranged in a diverging manner, so as to cover the relevant portion of substrate 40 (not shown). Collected plasma optical emission spectra are fed into the multi-channel spectrometer 310 from optical systems 300A-E, via respective optical fibers 320A-E. Optical systems 300A-E will be described in greater detail later. The embodiment of FIG. 4 is suitable for fast diagnostics, because of its ability to collect plasma optical emission spectra simultaneously.

Figure 5:
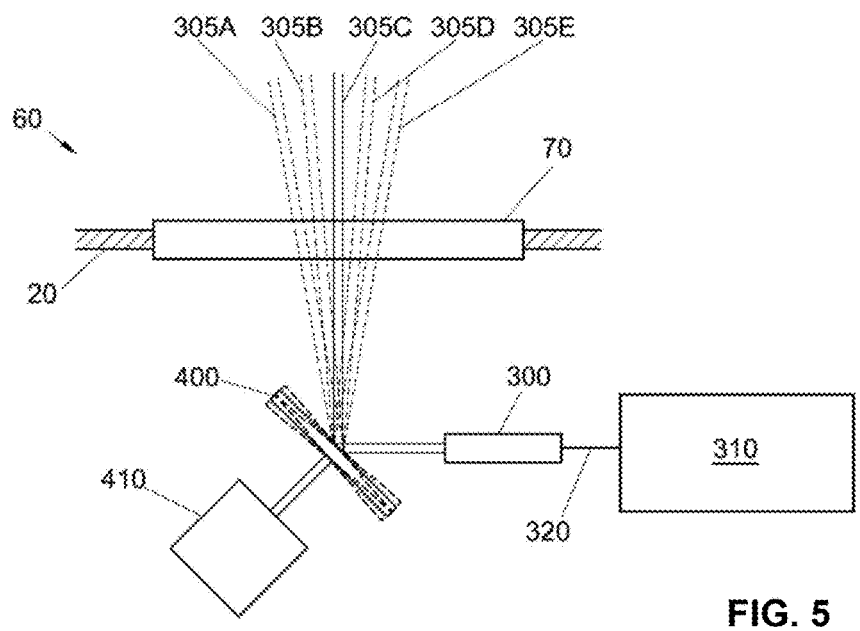
FIG. 5 is a schematic of an optical system for use in the OES measurement system, in accordance with another embodiment.

FIG. 5 shows an alternative embodiment in which a single channel spectrometer 310 is used and rays 305A-E are formed by a scanning mirror 400 which is controllably scanned to sweep out rays 305A-E while plasma optical emission spectra are acquired by the spectrometer 310 via a single optical system 300, which will be described in greater detail later. This embodiment is suitable for sequential collection of plasma optical emission spectra, and therefore is more suited for diagnostics of slower-evolving plasma processes. The scanning mirror 400 can be mounted and actuated by a galvanometer stage 410. Alternatively, the scanning mirror 400 may be mounted on and scanned by a stepper motor 410. The number of rays 305A-E here is shown as 5, but in practice it is determined by the settings in the controller software for controlling the galvanometer stage or stepper motor 410.

To ensure that a precise volume of space is sampled, the optical systems 300A-E of FIG. 4 and optical system 300 of FIG. 5 need to be configured such that rays 305A-E are collimated, with as small a divergence angle as can feasibly be achieved for a given target cost of the optical system.

Figure 6:
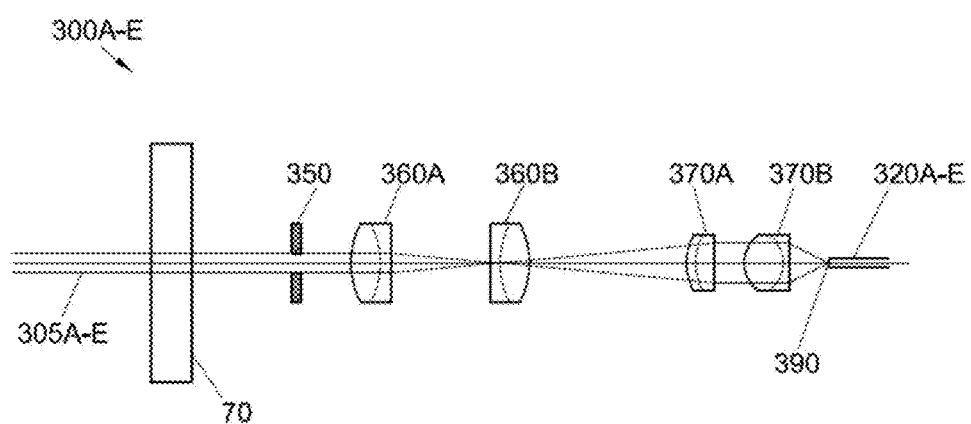
FIG. 6 is an expanded schematic view of an embodiment of an optical system in accordance with an embodiment.

An exemplary embodiment of optical systems 300A-E and 300 is shown in FIG. 6. The optical system 300A-E also known as a telecentric coupler, has the task of collecting plasma optical emission spectra from a volume of space within the plasma 50 defined by rays 305A-E, and directing the collected plasma optical emission spectra to the end 390 of an optical fiber 320A-E, or 320, so it can be transmitted to the spectrometers 310 of embodiments of FIG. 4 or 5. The diameter of the rays 305A-E is defined by an optional aperture 350, formed in a plate. In an alternative embodiment, other optical components, such as lenses can be used to define the diameter of the rays 305A-E. An example ray diameter is 4.5 mm but it can vary from about 1 mm to 20 mm, depending on the application. The collected rays 305A-E are passed through a combination of collection lenses 360A and 360B which in combination with the optional aperture define the rays 305A-E. The numerical aperture of the collection system and rays 305A-E is generally very low, for example, approximately 0.005, and the resultant rays 305A-E are essentially collimated, with minimal divergence angle. On the other end of optical system 300A-E or 300 is another pair of lenses, i.e. coupling lenses 370A and 370B, which serve to focus the collected optical emission spectra onto the end 390 of the optical fiber 320A-E, or 320. All lenses used in the system are preferably achromatic, or even apochromatic for more demanding applications, which ensures that the focal length of each lens does not vary with wavelength, such that the optical system 300A-E, or 300, operates satisfactorily over a large range of wavelengths, typically from 200 nm to 800 nm, but in some cases going as low as 150 nm. For better performance in the ultraviolet (UV) part of the spectrum, i.e. 350 nm and less, UV-grade materials are to be used for all optical components.

For every optical hardware configuration, it is important to know the optical efficiency w which is a weighting factor that applies to all points within rays 305A-E from which plasma optical emission spectra are acquired. The optical efficiency w can be determined by simulation, using optical design software, or by experiment using calibrated light sources and moving them across and along rays 305A-E to determine the efficiency of coupling of light from a given location within a ray 305A-E to the optical fiber end 390. The optical efficiencies w will be used in the algorithm for determining the spatial distribution of plasma optical emissions.

As mentioned before, the task of the plasma optical emission spectroscopy (OES) system 15 is the determination of the two-dimensional intensity distribution of the plasma optical emission, for each of M measured wavelengths $\lambda$.

For each ray 100 of FIG. 2, the ray being denoted mathematically by an index i, the collected optical detector output $D_i$ can be defined as $$D_i = \int_{l_{AB}} I(r, \theta) w(r, \theta) dl$$

where $I(r,\theta)$ is the plasma optical emission intensity at a location $(r,\theta)$ within and along the ray 100, and $w(r,\theta)$ is the optical efficiency for collection of light from location $(r,\theta)$ by optical detector i. The resultant optical detector output $D_i$ represents an integral of the product of these quantities along a straight path from point A to point B on the circumference of the substrate (see FIG. 2), the contributions from plasma outside the circumference of substrate 40 being neglected in this model (this is a valid assumption because the plasma density and thus plasma light emission is generally low in these areas).

In a plasma optical emission spectroscopy system 15 with N optical detectors and rays, or alternatively N scanned positions of rays 100, there are N collected intensities for each of M measured wavelengths $\lambda$. Therefore, to reconstruct a spatial distribution of plasma optical emission at one wavelength $\lambda$, a functional form with N parameters has to be assumed. Given the restricted number N of parameters, a judicious choice of basis functions for the distribution of plasma optical emission needs to be made. The selected basis functions need to vary both with radial coordinate r, and also the circumferential coordinate $\theta$ for them to be able to reproduce satisfactorily the circumferential variations of plasma emission across the substrate 40.

One class of basis functions particularly well suited to this task are Zernike polynomials $Z_p(r,\theta)$. Zernike polynomials are defined as a product of a term dependent on radial coordinate r and a term dependent on the circumferential coordinate $\theta$, i.e.

$$Z_p(r,\theta) = R(r)G(\theta)$$

Table 1 lists the first 18 order Zernike polynomials, herein denoted using commonly used mathematical notation $Z_n^m$.

TABLE 1

The first 18 order Zernike polynomials $Z_n^m$.

| Order | n | m | $R(r)G(\theta)$ |
|---|---|---|---|
| 0 | 0 | 0 | 1 |
| 1 | 1 | 1 | $2r \cos \theta$ |
| 2 | 1 | -1 | $2r \sin \theta$ |
| 3 | 2 | 2 | $\sqrt{6}r^2 \cos 2\theta$ |
| 4 | 2 | 0 | $\sqrt{3}(2r^2 - 1)$ |
| 5 | 2 | -2 | $\sqrt{6}r^2 \sin 2\theta$ |
| 6 | 3 | 3 | $\sqrt{8}r^3 \cos 3\theta$ |
| 7 | 3 | 1 | $\sqrt{8}(3r^3 - 2r) \cos \theta$ |
| 8 | 3 | -1 | $\sqrt{8}(3r^3 - 2r) \sin \theta$ |
| 9 | 3 | -3 | $\sqrt{8}r^3 \sin 3\theta$ |
| 10 | 4 | 4 | $\sqrt{10}r^4 \cos 4\theta$ |
| 11 | 4 | 2 | $\sqrt{10}(4r^3 - 3r^2) \cos 2\theta$ |
| 12 | 4 | 0 | $\sqrt{5}(6r^4 - 6r^2 + 1)$ |
| 13 | 4 | -2 | $\sqrt{10}(4r^3 - 3r^2) \sin 2\theta$ |
| 14 | 4 | -4 | $\sqrt{10}r^4 \sin 4\theta$ |
| 15 | 5 | 5 | $\sqrt{12}r^5 \sin 5\theta$ |
| 16 | 5 | 3 | $\sqrt{12}(5r^5 - 4r^3) \cos 3\theta$ |
| 17 | 5 | 1 | $\sqrt{12}(10r^5 - 12r^3 + 3r) \cos \theta$ |

In general, other basis functions can be chosen in this application, as long as they are orthogonal and as long as their derivatives are continuous over the unit circle, just as is the case with Zernike polynomials. However, Zernike polynomials are preferred in this application because of their property that a relatively small number of terms can be used to describe quite complex variations of a function in polar coordinates, both radial and circumferential.

Substituting Zernike polynomials $Z_p(r,\theta)$ into the collected detector output results in $$D_i = \int_A^B w(r, \theta) \sum_{p=1}^N a_p Z_p(r, \theta) dl = \int_A^B w(r, \theta) \sum_{p=1}^N a_p R_p(r) G(\theta) dl$$

where $\alpha_p$ are fitting parameters associated with every basis function, i.e. Zernike polynomial order.

Now that the collected detector output $D_i$ is defined in terms of the selected basis functions, fitting parameters, and optical efficiency, the problem of determining the fitting parameters $\alpha_p$ of $D_i$ is reduced to minimizing the following, i.e. solving the least squares problem $$\min\left\{\sum_{i=1}^{N}(D_i - D_i^{measured})^2\right\}$$

or $$\min\left\{\sum_{i=1}^{N}\left(\int_A^B w(r,\theta)\sum_{p=1}^{N}\alpha_p R_p(r)G(\theta)dl - D_i^{measured}\right)^2\right\}$$

where $D_i^{measured}$ represent the measured plasma optical spectra intensities at ray i. This minimization algorithm needs to be repeated for each of M measured wavelengths $\lambda$. Many methods are known in the art for solving this least squares problem. Because the dimension of the least squares problem is relatively small it can be efficiently solved for all wavelengths, for each instant in time that plasma optical emission spectra are measured; and furthermore such calculations can be repeated in rapid succession enabling the determination of rapidly evolving two-dimensional distributions of plasma optical emissions for large numbers M of wavelengths. From these one can then determine the time-evolving two-dimensional distributions of chemical species concentrations across the substrate 40, which can be used for endpoint detection, fault detection, process development, processing tool development, etc.

Figure 7:
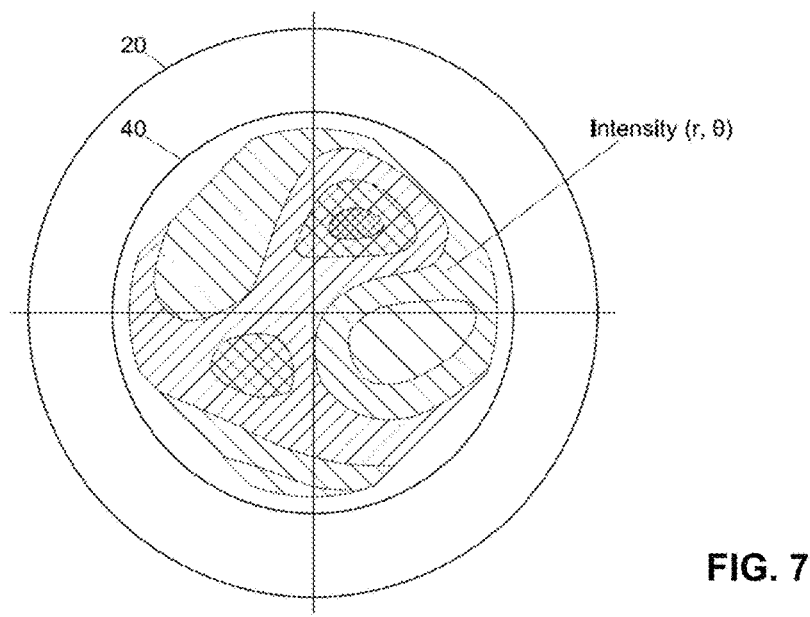
FIG. 7 is an exemplary two-dimensional distribution of plasma optical emission measured using the OES measurement system and associated method in accordance with an embodiment.

FIG. 7 shows an example of one such plasma optical emission intensity distribution determined with the method in accordance with an embodiment of the invention. The depicted distribution clearly shows good capture of both radial and circumferential variations in the plasma optical emission intensity, despite a relatively low number of terms, i.e. N=18.

Figure 8:
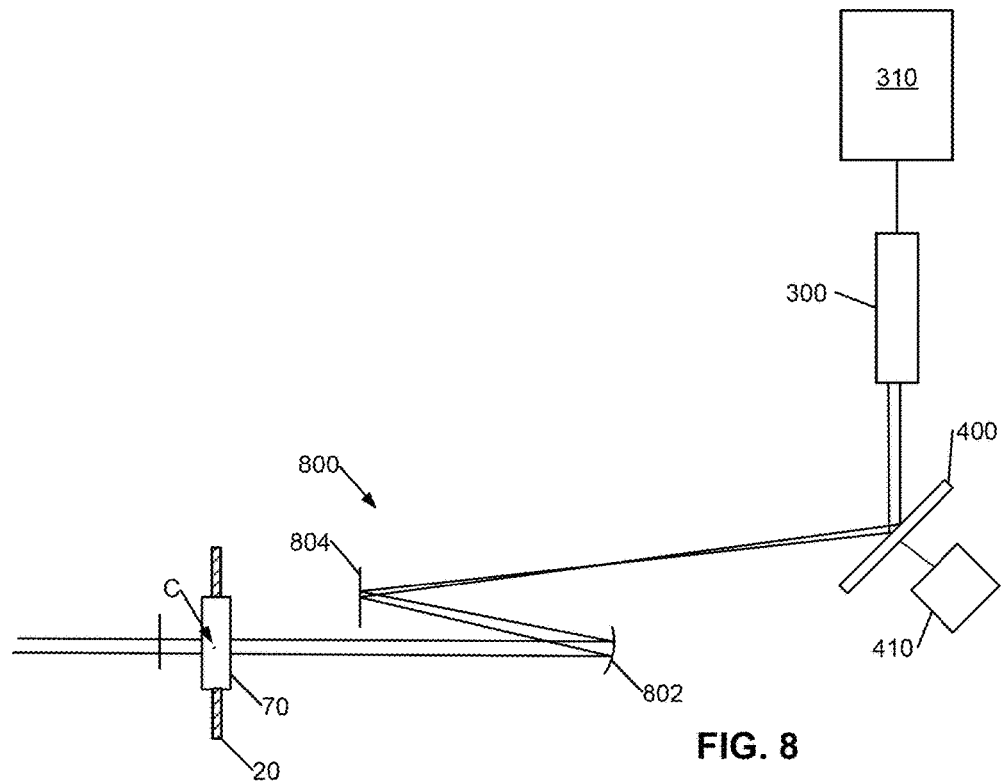
FIG. 8 is a schematic of an optical system for use in the OES measurement system, in accordance with another embodiment.

FIG. 8 shows an alternative embodiment in which a single channel spectrometer 310 is used. Rays 305A-E are formed by the scanning mirror 400 and a mirror system 800 which moves a center of rotation of the rays 305A-E from a location of the stepper motor 410 associated with the scanning mirror 400 to the optical window 70 or substantially near the optical window 70 as indicated by point C in FIG. 8 (i.e., point C shows the center of rotation). The optical window 70 is typically small (i.e., one inch in diameter) thus in order to sweep out rays 305A-E across the plasma 50 (e.g., an angle $\theta_{max}=25°$ of a center axis of the plasma processing chamber 20), rays 305A-E have a minimal excursion at the optical window 70. Therefore, the center of rotation of rays 305A-E is configured to be substantially near or at the optical window 70. Using the configuration described herein, using a window having a dimension of 68.5 mm×8 mm or larger is possible. The window dimension (i.e., upper limit) is limited by factors such as contamination, chamber UV and RF leakage, and available space at the wall of the plasma processing chamber 20. In one implementation, the window may have a rectangular shape with the large dimension in a plane corresponding to the plane of scanning of the beam. That has the advantage of minimizing the size of the window while satisfying leakage and space requirements.

The scanning mirror 400 is controllably scanned to sweep out rays 305A-E using the stepper motor 410 while the plasma optical emission spectra are acquired by the spectrometer 310 via a single optical system 300.

The mirror system 800 may include a transfer mirror 802 and a fold mirror 804. Each collected ray 305A-E or 65 (i.e., optical signal from a plasma with collected ray 305) is transmitted by the transfer mirror 802 which reflects the collected ray 305 and transfers the collected ray 305 to the fold mirror 804. The fold mirror 804 reflects the collected ray 305 from horizontal (azimuthal) to vertical concentric and transmit the collected ray 305 to the scanning mirror 400 which reflects the collected ray 305 to the optical system 300. The mirror system 800 and the optical system 300 are stationary. The mirror system 800, the scanning mirror 400, the optical system 300, and the spectrometer 310 may be mounted proximate to the plasma processing chamber 20.

As the scanning mirror 400 is swept, a high spatial resolution of the spatial distribution of chemical species concentrations is obtained. For example, the scanning mirror 400 may be swept slowly while the plasma optical emission spectra is acquired. The acquired plasma optical emission spectra is associated with any position between $-\theta_{max}°,+\theta_{max}°$. Thus, using the scanning setup described herein, a very precise spatial resolution may be obtained.

Figure 9:
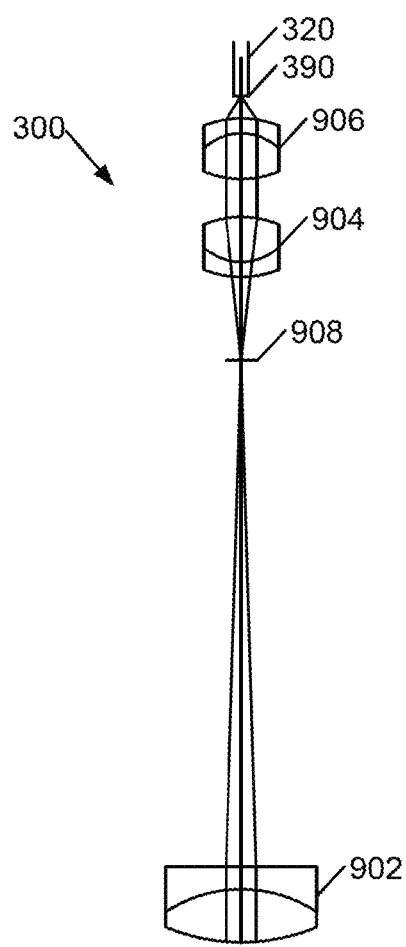
FIG. 9 is an expanded schematic view of an embodiment of an optical system in accordance with another embodiment.

FIG. 9 is an expanded schematic view of an embodiment of the optical system 300 of FIG. 8 in accordance with an embodiment. The optical system 300 has the task of collecting plasma optical emission spectra from a volume of space within the plasma 50 defined by collected rays 305, and directing the collected plasma optical emission spectra to the end 390 of the optical fiber 320, so it can be transmitted to the spectrometer 310 as described previously herein. Optical system 300 includes a telecentric coupler with a small NA. The collected scanning rays sizes can vary from about 3 to 5 mm in diameter along the collection path.

The collected ray 305 (i.e., reflected from the scanning mirror 400) is passed through a first collection lens 902. Then, the rays may be passed through a telecentric aperture 908, for example having a diameter of 600 μm. Then, two coupling lenses 904 and 906, serve to focus the collected optical emission spectra onto the end 390 of the optical fiber 320. In one example, the optical fiber 320 has a diameter of 600 μm. The collection system 300 may also include an optional filter positioned between the two coupling lenses 904 and 906.

The numerical aperture of the collection system 300 is very low, for example 0.005. Lenses 902, 904, 906 are achromatic lenses having effective focal lengths of 30 mm, 12.5 mm, and 12.5 mm, and diameters of 12.5 mm, 6.25 mm, and 6.25 mm, respectively.

Referring back to FIG. 8, the scanning mirror 400 may have a dimension of at least 10 mm×10 mm. The transfer mirror 802 may be a spherical mirror. The scanning mirror 400 and the transfer mirror 802 may have an Aluminum coating, a Silicon Monoxide (SiO) overcoat, or a multilayer film of dielectrics on top of aluminum to increase the reflectance in certain wavelength regions (e.g., UV). The transfer mirrors 802 radius may be between 100 mm to 120 mm. In one implementation, the transfer mirror's 802 radius is 109.411 mm. The transfer mirror 802 may be positioned at a distance of 68.4 mm from an outer edge of the optical window 70. The fold mirror 804 may be positioned at a distance of 71.5 mm from the plane of the scanning mirror 400.

Spectrometer 310 may be an ultra broad band (UBB) high resolution spectrometer with a spectral resolution of 0.4 nm and having a wavelength range between 200 nm-1000 nm.

Figure 10:
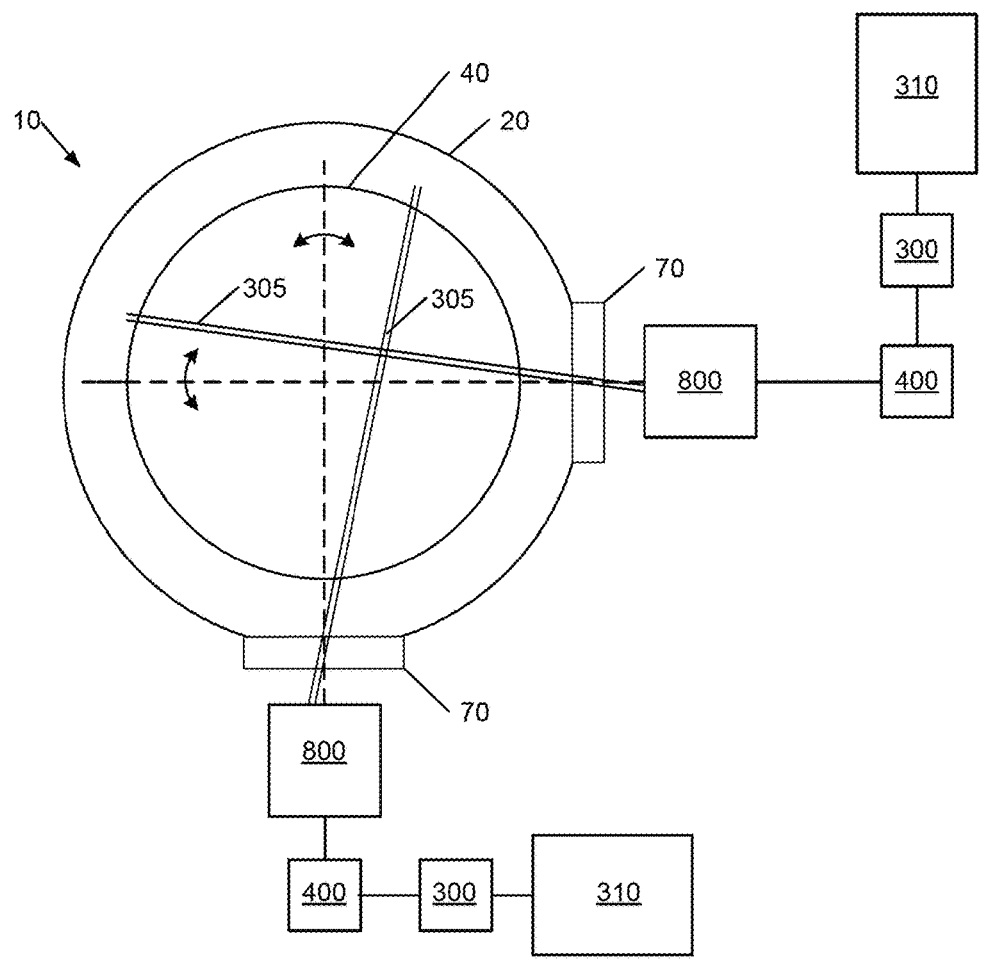
FIG. 10 is a top view schematic of the plasma processing system equipped with the optical system of FIG. 8.

FIG. 10 is a top view schematic of the plasma processing system equipped with the optical system of FIG. 8. The plasma processing chamber 20 may be equipped with two optical systems of FIG. 8. The optical system is referred to as a scanning module. Each scanning module may be configured to collect data from X to Y ray positions. In one implementation, each scanning module may be configured to collect data from 5 to 50 ray positions which provide better accuracy to detect events with high spatial resolution. In FIG. 10, one position of ray 305 is shown. As described previously herein, scan angle of rays 305 may vary from $-\theta_{max}°, +\theta_{max}°$ (e.g., $\theta_{max}=25°$ or 30°). Data from spectrometers 310 are processed as described previously herein to obtain the two dimensional (2D) OES intensity distribution. Each module may include a single channel spectrometer 310, or alternatively a single spectrometer having two channels may be used for the two scanning modules. Additional scanning modules may also be used to provide higher spatial resolution. Optical windows 70 (i.e., optical window 70 of each scanning module) may be located on the side wall of the plasma processing chamber 20 perpendicular or substantially perpendicular to each other. Depending on the configuration of plasma processing chamber 20, the optical windows 70 may be quartz, fused silica, or sapphire depending on the application and how aggressive the chemistry of the plasma.

Figure 11:
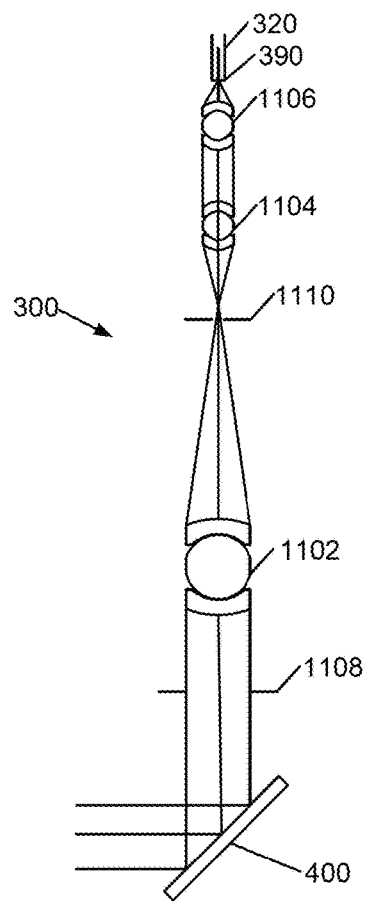
FIG. 11 is an expanded schematic view of an embodiment of an optical system in accordance with another embodiment.

FIG. 11 is an expanded schematic view of an embodiment of the optical system 300 of FIG. 5 or FIG. 8. The optical system 300 has the task of directing the reflected collected plasma optical emission spectra from the scanning mirror 400 to the end 390 of the optical fiber 320, so it can be transmitted to the spectrometer 310 as described previously herein. The collected ray 305 is passed through a collection lens which may be a triplet lens 1102, for example having an effective focal length of 40 mm. The collected ray 305 may be passed through an optional mask aperture 1108, for example having a diameter of 7 mm. The mask aperture 1108 may be positioned between the scanning mirror 400 and the triplet lens 1102. Then, the collected ray 305 may be passed through an optional telecentric aperture 1110, for example having a diameter of 1.20 mm. In an alternative embodiment, other optical components, such as lenses can be used to define the diameter of the rays 305.

Two coupling triplet lenses 1104 and 1106, serve to focus the collected optical emission spectra onto the end 390 of the optical fiber 320. In one implementation, the coupling triplet lenses 1104 and 1106 may be triplet lenses having effective focal lengths of 15 mm. The effective focal lengths of the coupling triplet lenses 1104 and 1106 is a function of a type and a diameter of the optical fiber 320.

All lenses used in the system are preferably achromatic, or even apochromatic for more demanding applications, which ensures that the focal length of each lens does not vary with wavelength, such that the optical system 300A-E, or 300, operates satisfactorily over a large range of wavelengths, typically from 200 nm to 1000 nm, but in some cases going as low as 150 nm. For better performance in the UV part of the spectrum, i.e. 350 nm and less, UV-grade materials such as quartz, fused silica, Calcium fluoride (CaF2) are used for all optical components.

Figure 12:
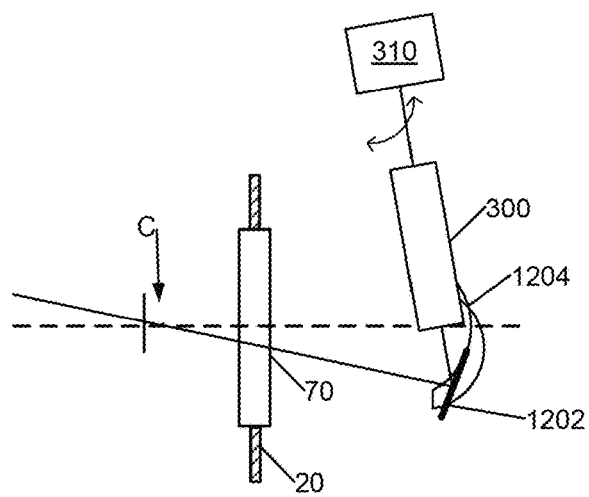
FIG. 12 is a schematic of an optical system for use in the OES measurement system, in accordance with another embodiment.

FIG. 12 is a schematic of an alternative embodiment in which a single channel spectrometer 310 is used. The plasma optical emission spectra can be acquired sequentially using one or two modules. Each module may include a linear arc stage 1204. The spectrometer 310, the optical system 300, and a fold mirror 1202 are mounted on the linear arc stage 1204. The fold mirror 1202 is positioned to receive the collected ray 305 from the plasma processing chamber 20 and to reflect the collected ray 305 to the optical system 300. The linear arc stage 1204 is controllably scanned to sweep out collected rays 305 while the plasma optical emission spectra are acquired by the spectrometer 310 via a single optical system 300. The linear arc stage 1204 may be controlled via the controller 80. Point C in FIG. 12 indicates the center of rotation of the linear arc stage 1204. The single optical system 300 may be that shown and described in FIG. 9 or FIG. 11. In one implementation, the linear arc stage 1204 may have a scanning angle of 85° and a length of 163.2 mm. The linear scanning speed may vary from 0.35 m/s to 2.2 m/s. Thus, the scanning speed may be adjusted to optimize a tradeoff between spatial resolution and speed depending on the application of the plasma optical emission spectroscopy system 15.

In further embodiments of optical system 300 of FIGS. 6, 9, and 11, other optical components may be used, such as mirrors, prisms, lenses, spatial light modulators, digital micromirror devices, and the like, to steer the collected rays 305. The configuration and component layout of the optical system 300 of FIGS. 4-6, and FIGS. 8-12 do not necessary need to be as shown exactly in FIGS. 4-6, and FIGS. 8-12, but the collected rays 305 can be folded and steered by way of additional optical components to facilitate packaging the plasma optical emission spectroscopy system 15 into a compact packaging suitable for mounting on the wall of the plasma processing chamber 20.

The inventors performed several experiments to reconstruct patterns of optical emission distribution and to compare the reconstructed patterns to etch patterns.

Figure 13:
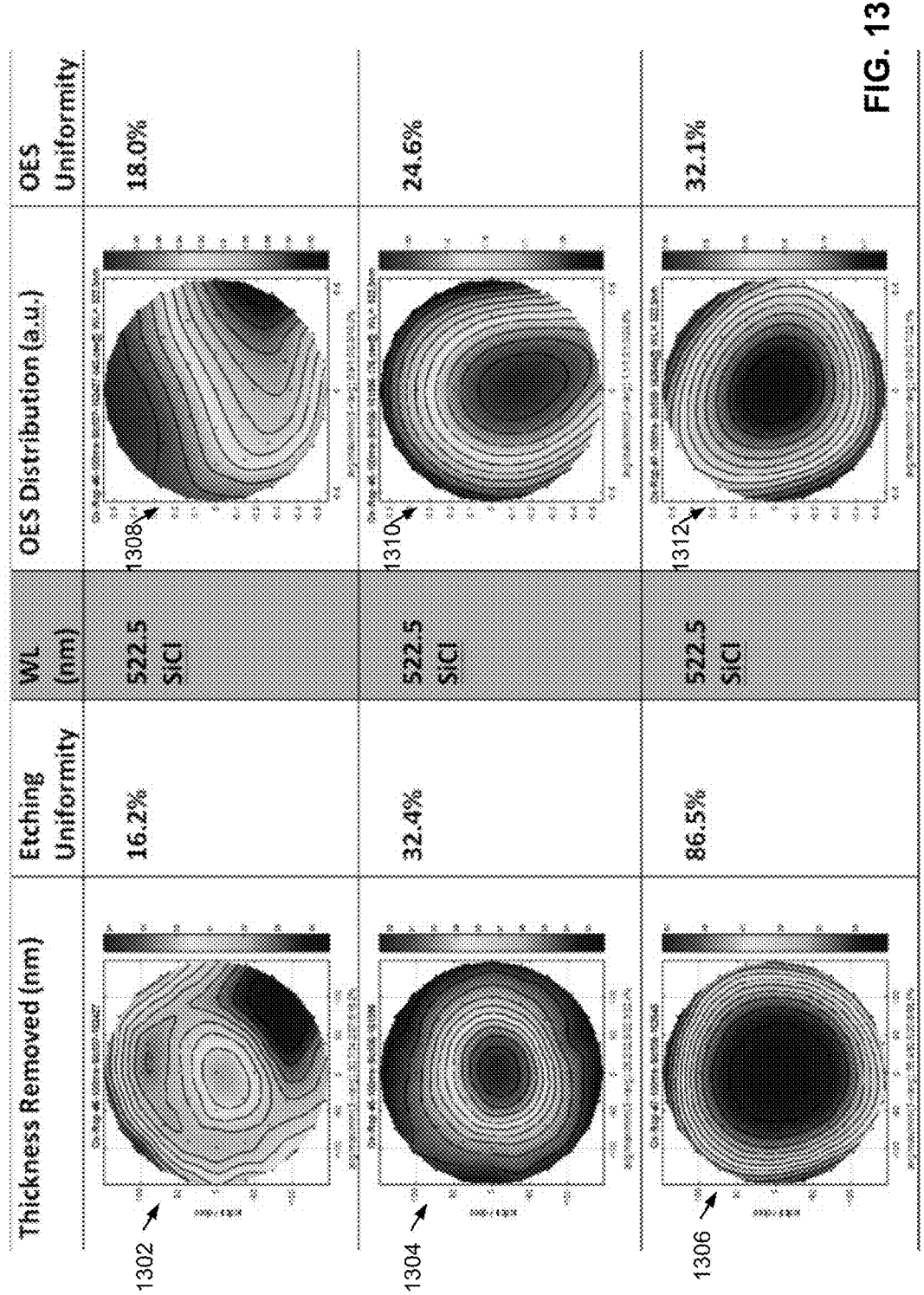
FIG. 13 is a schematic that shows exemplary results of reconstructed patterns of optical emission intensity.

FIG. 13 is a schematic that shows exemplary results of reconstructed patterns of optical emission intensity. The intensity of an emission line (i.e., 522.45 nm for silicon chloride) indicates the concentration of silicon chloride (SiCl) which in turn is associated with the intensity of local etching on the substrate 40. FIG. 13 shows a comparison between an actual etch rate and an actual distribution of the optical emission acquired by the plasma OES system 15 described herein at 522.5 nm. Plots 1302, 1304, and 1306 show actual etching rate for various samples at various plasma processing conditions. Plots 1308, 1310, and 1312 show the reconstructed optical emission distribution for the samples associated with plots 1302, 1304, and 1306, respectively.

Using the apparatus and methodologies describes herein the etching uniformity may be monitored. For example, the apparatus may be used during process development to monitor the etching uniformity for various plasma processing conditions without transferring the substrate to another apparatus which makes the development of various processes faster.

The results show strong correlation between the etching thickness and the reconstructed OES distribution given by plasma etching involved species, including both reactants and products. The uniformity of OES distribution and Oxide etching profile follows the same trend, for example plot 1302 compared to plot 1308. Substrate with better etching uniformity shows lower correlation with OES distribution (e.g., plot 1306 compared to plot 1302).

Figure 14:
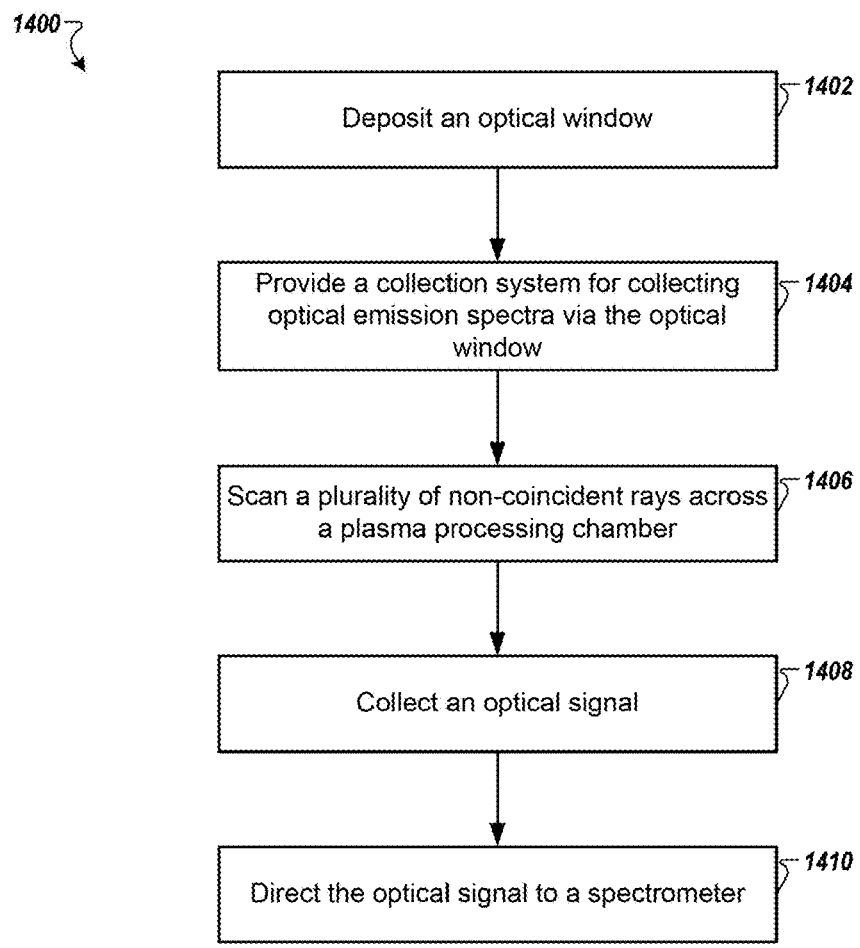
FIG. 14 is a flowchart that shows a method for optical emission measurement according to one example.

FIG. 14 is a flowchart that shows a method 1400 for optical emission measurement according to one example. At 1402, an optical window is deposited at a wall of a plasma processing chamber (e.g., the plasma processing chamber 20). At 1404, a collection system is provided for collecting plasma optical emission spectra through the optical window. The collection system may include a mirror and a telecentric coupler. The telecentric coupler may include at least one collection lens (e.g., collection lens 360A and 360B) and at least one coupling lens (e.g., coupling lenses 904 and 906 of FIG. 9). At 1406, a plurality of non-coincident rays is scanned across the plasma processing chamber using the mirror. The scanning may be controlled by the controller 80. At 1408, an optical signal is collected from a plasma via the telecentric coupler. At step 1410, the optical signal is directed to a spectrometer for measuring the plasma optical emission spectra.

Persons skilled in the relevant art can appreciate that many modifications and variations are possible in light of the above teaching. Persons skilled in the art will recognize various equivalent combinations and substitutions for various components shown in the figures. It is therefore intended that the scope of the invention be limited not by this detailed description, but rather by the claims appended hereto.

The above disclosure also encompasses the embodiments listed below.

(1) A method for optical emission measurement, comprising depositing an optical window at a wall of a plasma processing chamber; providing a collection system for collecting plasma optical emission spectra through the optical window, the collection system including a mirror and a telecentric coupler; scanning a plurality of non-coincident rays across the plasma processing chamber using the mirror; collecting an optical signal from a plasma via the telecentric coupler; and directing the optical signal to a spectrometer for measuring the plasma optical emission spectra.

(2) The method of feature (1), wherein the telecentric coupler includes at least one collection lens; and at least one coupling lens.

(3) The method of feature (2), in which the at least one collection lens or the at least one coupling lens are achromatic lenses.

(4) The method of feature (2), in which the telecentric coupler further includes: an aperture disposed between the at least one collection lens and the at least coupling lens for defining a diameter of the plurality of non-coincident rays.

(5) The method of any of features (1) to (4), in which the mirror is a scanning mirror.

(6) The method of feature (5), in which the scanning mirror is mounted on and scanned by a galvanometer scanning stage.

(7) The method of feature (5), in which the scanning mirror is mounted on and scanned by a stepper motor.

(8) The method of feature (5), in which the collection system further includes a mirror system for shifting a center of rotation of the plurality of non-coincident rays to the optical window or near the optical window.

(9) The method of feature (8), in which the mirror system includes a transfer mirror; a fold mirror; and in which the transfer mirror is configured to transfer the collected signal to the fold mirror and the fold mirror is configured to transfer the collected signal to the mirror.

(10) The method of feature (1), in which the telecentric coupler includes a collection triplet lens configured to collect the optical signal from the mirror; and two coupling triplet lenses configured to focus the collected signal into an end of an optical fiber coupled to the spectrometer.

(11) The method of feature (1), further comprising collecting the plasma optical emission spectra via a second optical window disposed at the wall of the plasma processing chamber using a second collection system. The center axis of the second optical window is perpendicular to the center axis of the optical window.

(12) The method of feature (1), in which the collection system further includes a linear arc stage holding the mirror, the telecentric coupler, and the spectrometer, the linear arc stage being configured to move radially with respect to a center axis of the optical window causing the plurality of non-coincident rays to scan across the plasma processing chamber.

(13) The method of feature (12), in which the mirror is a fold mirror.

(14) The method of any of features (1) to (13), in which the plurality of non-coincident rays are scanned 25° of a center axis of the optical window across the plasma processing chamber.

(15) The method of any of features (1) to (14), in which the spectrometer is an ultra broadband high resolution spectrometer.

(16) The method of any of features (1) to (15), in which the collection system has a low numerical aperture.

(17) The method of any of features (1) to (14), in which the optical signal is collected from 21 non-coincident rays.

What is claimed is:

1. An apparatus for optical emission measurement, the apparatus comprising:
    a plasma processing chamber;
    an optical window disposed on a wall of the plasma processing chamber; and
    a collection system for collecting a plasma optical emission spectra through the optical window, the collection system including:
        a mirror system configured to scan a plurality of non-coincident rays across the plasma processing chamber; and
        a telecentric coupler for collecting an optical signal from a plasma and directing the optical signal to a spectrometer for measuring the plasma optical emission spectra, wherein a center of rotation of the plurality of non-coincident rays is substantially at the optical window.

2. The apparatus of claim 1, wherein the telecentric coupler includes:
    at least one collection lens; and
    at least one coupling lens.

3. The apparatus of claim 2, wherein the at least one collection lens or the at least one coupling lens are achromatic lenses.

4. The apparatus of claim 2, wherein the telecentric coupler further includes:
    an aperture disposed between the at least one collection lens and the at least coupling lens for defining a diameter of the plurality of non-coincident rays.

5. The apparatus of claim 1, wherein the mirror system includes a scanning mirror.

6. The apparatus of claim 5, wherein the scanning mirror is mounted on and scanned by a galvanometer scanning stage.

7. The apparatus of claim 5, wherein the scanning mirror is mounted on and scanned by a stepper motor.

8. The apparatus of claim 5, wherein the mirror system includes:
    a transfer mirror;
    a fold mirror; and
    wherein the transfer mirror is configured to transfer the collected signal to the fold mirror and the fold mirror is configured to transfer the collected signal to a scanning mirror.

9. The apparatus of claim 1, wherein the telecentric coupler includes:
   a collection triplet lens configured to collect the optical signal from the mirror system; and
   two coupling triplet lenses configured to focus the collected signal into an end of an optical fiber coupled to the spectrometer.

10. The apparatus of claim 1, further comprising:
    a second optical window; and
    a second collection system for collecting the plasma optical emission spectra through the second optical window disposed at the wall of the plasma processing chamber, the second optical window having a center axis perpendicular to the center axis of the optical window.

11. The apparatus of claim 1, wherein the collection system further includes:
    a linear arc stage holding the mirror system, and the telecentric coupler, the linear arc stage being configured to move radially with respect to a center axis of the optical window causing the plurality of non-coincident rays to scan across the plasma processing chamber.

12. The apparatus of claim 11, wherein the mirror system includes a fold mirror.

13. The apparatus of claim 1, wherein the plurality of non-coincident rays are scanned 25° of a center axis of the optical window across the plasma processing chamber.

14. The apparatus of claim 1, wherein the collection system has a low numerical aperture.

15. The apparatus of claim 1, wherein the optical signal is collected from 21 non-coincident rays.

16. A system for plasma processing, comprising:
    a plasma processing chamber;
    an optical window disposed on a wall of the plasma processing chamber;
    a collection system for collecting plasma optical emission spectra through the optical window;
    a spectrometer coupled to the collection system for measuring the plasma optical emission spectra; and
    wherein the collection system includes
        a mirror system configured to scan a plurality of non-coincident rays across the plasma processing chamber, and
        a telecentric coupler for collecting an optical signal from a plasma and directing the optical signal to the spectrometer, wherein a center of rotation of the plurality of non-coincident rays is substantially at the optical window.

17. A method for optical emission measurement, comprising:
    depositing an optical window at a wall of a plasma processing chamber;
    providing a collection system for collecting plasma optical emission spectra through the optical window, the collection system including a mirror system and a telecentric coupler;
    scanning a plurality of non-coincident rays across the plasma processing chamber using the mirror system;
    collecting an optical signal from a plasma via the telecentric coupler; and
    directing the optical signal to a spectrometer for measuring the plasma optical emission spectra, wherein a center of rotation of the plurality of non-coincident rays is substantially at the optical window.

18. The method of claim 17, wherein the mirror system includes at least a transfer mirror and a fold mirror.

19. The system of claim 16, wherein the spectrometer is an ultra broadband high resolution spectrometer.

20. The system of claim 16, wherein the plurality of non-coincident rays are scanned 30° of a center axis of the optical window across the plasma processing chamber.

* * * * *